United States Patent
Boone et al.

(10) Patent No.: US 11,502,009 B2
(45) Date of Patent: Nov. 15, 2022

(54) DIE CARRIER PACKAGE AND METHOD OF FORMING SAME

(71) Applicant: Medtronic, Inc., Minneapolis, MN (US)

(72) Inventors: Mark R. Boone, Gilbert, AZ (US); Mark E. Henschel, Phoenix, AZ (US)

(73) Assignee: Medtronic, Inc., Minneapolis, MN (US)

(*) Notice: Subject to any disclaimer, the term of this patent is extended or adjusted under 35 U.S.C. 154(b) by 26 days.

(21) Appl. No.: 17/165,005

(22) Filed: Feb. 2, 2021

(65) Prior Publication Data
US 2021/0159131 A1 May 27, 2021

Related U.S. Application Data

(62) Division of application No. 16/175,314, filed on Oct. 30, 2018, now Pat. No. 10,950,511.

(51) Int. Cl.
*H01L 21/00* (2006.01)
*H01L 23/12* (2006.01)
(Continued)

(52) U.S. Cl.
CPC .......... *H01L 23/12* (2013.01); *H01L 21/4846* (2013.01); *H01L 21/4853* (2013.01);
(Continued)

(58) Field of Classification Search
CPC ......... H01L 23/00; H01L 23/12; H01L 23/31; H01L 23/498; H01L 23/538; H01L 23/3121; H01L 23/49838; H01L 23/49866; H01L 23/49816; H01L 23/5386; H01L 23/15; H01L 23/49894; H01L 23/5389;
(Continued)

(56) References Cited

U.S. PATENT DOCUMENTS

| 5,266,794 A | 11/1993 | Olbright et al. |
| 6,174,749 B1 | 1/2001 | Yuen et al. |

(Continued)

FOREIGN PATENT DOCUMENTS

| TW | 201037793 | 10/2010 |
| WO | 2017/171813 | 10/2017 |

OTHER PUBLICATIONS

Hunt et al., "Synergy between 2.5/3D Development and Hybrid 3D Wafer Level Fanout," ASE Group Kaohsiung, 10 pages.

(Continued)

*Primary Examiner* — Chuong A Luu
(74) *Attorney, Agent, or Firm* — Mueting Raasch Group (57) ABSTRACT

Various embodiments of a die carrier package and a method of forming such package are disclosed. The package includes one or more dies disposed within a cavity of a carrier substrate, where a first die contact of one or more of the dies is electrically connected to a first die pad disposed on a recessed surface of the cavity, and a second die contact of one or more of the dies is electrically connected to a second die pad also disposed on the recessed surface. The first and second die pads are electrically connected to first and second package contacts respectively. The first and second package contacts are disposed on a first major surface of the carrier substrate adjacent the cavity.

20 Claims, 7 Drawing Sheets

(51) Int. Cl.
  *H01L 21/48* (2006.01)
  *H01L 21/52* (2006.01)
  *H01L 21/56* (2006.01)
  *H01L 23/31* (2006.01)
  *H01L 23/498* (2006.01)
  *H01L 23/538* (2006.01)
  *H01L 23/00* (2006.01)
  *H01L 31/12* (2006.01)
  *A61B 5/00* (2006.01)
  *A61N 1/375* (2006.01)
  *H01L 31/0203* (2014.01)
  *H01L 33/48* (2010.01)

(52) U.S. Cl.
  CPC ............. *H01L 21/52* (2013.01); *H01L 21/56* (2013.01); *H01L 23/3121* (2013.01); *H01L 23/49816* (2013.01); *H01L 23/49838* (2013.01); *H01L 23/49866* (2013.01); *H01L 23/5386* (2013.01); *H01L 24/48* (2013.01); *H01L 24/85* (2013.01); *H01L 31/125* (2013.01); *A61B 5/686* (2013.01); *A61N 1/375* (2013.01); *H01L 31/0203* (2013.01); *H01L 33/483* (2013.01); *H01L 2224/48248* (2013.01)

(58) Field of Classification Search
  CPC . H01L 23/3128; H01L 23/28; H01L 23/3192; H01L 23/495; H01L 23/49503; H01L 23/552; H01L 23/556; H01L 31/12; H01L 31/125; H01L 24/48; H01L 24/85; H01L 21/78; H01L 21/786; H01L 21/566; H01L 21/565; H01L 21/568; H01L 21/481; H01L 21/4807; H01L 21/4867; H01L 21/48; H01L 21/52; H01L 21/56; H01L 21/4846; H01L 21/4853; H01L 2224/8185; H01L 2224/48491; H01L 2924/181; H01L 2924/186; H01L 2225/107; H01L 2225/1041; H01L 2225/06551; H01L 2225/06506; H01L 31/0203; H01L 33/483; H01L 24/16; H01L 24/32; H01L 24/73; H01L 24/97; H01L 24/01; H01L 24/83
  USPC ........................................................ 438/106
  See application file for complete search history.

(56) References Cited

U.S. PATENT DOCUMENTS

| | | |
|---|---|---|
| 6,259,121 B1 | 7/2001 | Lemoff et al. |
| 6,636,544 B2 | 10/2003 | Baillargeon et al. |
| 6,953,702 B2 | 10/2005 | Miller et al. |
| 8,313,962 B2 | 11/2012 | Lott et al. |
| 8,664,756 B2 | 3/2014 | Boone et al. |
| 8,743,923 B2 | 6/2014 | Geske et al. |
| 9,057,853 B2 | 6/2015 | Lau et al. |
| 9,065,254 B2 | 6/2015 | Geske et al. |
| 10,463,285 B2 | 11/2019 | Boone et al. |
| 2003/0116859 A1 | 6/2003 | Hashimoto |
| 2005/0046035 A1* | 3/2005 | Egawa ............... H01L 23/13 257/777 |
| 2017/0272081 A1 | 9/2017 | Chiang et al. |
| 2018/0012853 A1 | 1/2018 | Lin et al. |
| 2018/0279924 A1 | 10/2018 | Kuhn |

OTHER PUBLICATIONS

Lin et al., "Advanced 3D eWLB-PoP (embedded Wafer Level Ball Grid Array—Package on Package) Technology," 2016 IEEE 66th Electronic Components and Technology Conference, Singapore, 6 pages.

* cited by examiner

DIE CARRIER PACKAGE AND METHOD OF FORMING SAME

RELATED APPLICATIONS

This application is a divisional of U.S. patent application Ser. No. 16/175,314, filed Oct. 30, 2018, which is incorporated herein by reference.

TECHNICAL FIELD

This disclosure generally relates to die carrier packages and methods of forming such packages.

BACKGROUND

IMDs for monitoring a physiological condition and/or delivering a therapy can include one or more physiological sensors. Such sensors can provide one or more signals related to one or more physiological conditions of a patient state. Examples of such IMDs include heart monitors, pacemakers, implantable cardioverter defibrillators (ICDs), myostimulators, neurological stimulators, drug delivery devices, insulin pumps, glucose monitors, etc.

Optical sensors may be employed in IMDs as physiological sensors configured to detect changes in light modulation by, for example, a body fluid or tissue measurement volume due to a change in a physiological condition in the body fluid or tissue. Such optical sensors can be used, for example, to detect changes in metabolite levels in the blood, such as oxygen saturation levels or glucose levels, or changes in tissue perfusion. A typical optical sensor can include one or more light sources and one or more detectors that are adapted to detect light emitted by the light sources and modulated by, e.g., body fluid or tissue measurement volume.

Monitoring such physiological conditions provides useful diagnostic measures that can be used in managing therapies for treating a medical condition. For example, a decrease in blood oxygen saturation or tissue perfusion may be associated with insufficient cardiac output or respiratory function. Thus, monitoring such conditions may allow an implantable medical device to respond to a decrease in oxygen saturation or tissue perfusion, for example, by delivering electrical stimulation therapies to the heart to restore normal hemodynamic function.

SUMMARY

The techniques of this disclosure generally relate to a die carrier package and a method of forming such package. The package can include one or more dies disposed within a cavity of a carrier substrate, where a first die contact of one or more of the dies is electrically connected to a first die pad disposed on a recessed surface of the cavity, and a second die contact of one or more of the dies is electrically connected to a second die pad also disposed on the recessed surface. The first and second die pads are electrically connected to first and second package contacts respectively. The first and second package contacts are disposed on a first major surface of the carrier substrate adjacent the cavity. In one or more embodiments, the first and second package contacts and an active surface of the die are disposed such that the package can be electrically connected to a major surface of a substrate so that the active surface of the die faces the major surface and the first and second package contacts are in contact with the same major surface. In embodiments where the die is adapted to emit electromagnetic radiation from its active surface, such radiation will be emitted in a direction away from the first major surface of the carrier substrate.

In one example, aspects of this disclosure relate to a die carrier package. The package includes a carrier substrate having a first major surface, a second major surface, and a cavity disposed in the first major surface. The cavity includes a recessed surface. The package further includes a first package contact disposed on the first major surface of the carrier substrate adjacent the cavity and electrically connected to a first die pad disposed on the recessed surface via a first conductor, a second package contact disposed on the first major surface of the carrier substrate adjacent the cavity and electrically connected to a second die pad disposed on the recessed surface via a second conductor, and a die disposed within the cavity of the carrier substrate and having a first die contact disposed on an active surface of the die and a second die contact disposed on a major surface of the die that faces the recessed surface and that is opposed to the active surface. The first die contact is electrically connected to the first die pad and the second die contact is electrically connected to the second die pad.

In another example, aspects of this disclosure relate to a method of forming a die carrier package. The method includes forming a cavity in a first major surface of a carrier substrate, where the cavity includes a recessed surface; forming a patterned conductive layer on the recessed surface of the cavity and the first major surface of the carrier substrate, where the first patterned conductive layer includes first and second package contacts disposed on the first major surface of the carrier substrate adjacent the cavity and first and second die pads disposed on the recessed surface of the recessed surface, and where the first package contact is electrically connected to the first die pad by a first conductor and the second package contact is electrically connected to the second die pad by a second conductor; and disposing a die within the cavity. The method further includes electrically connecting a first die contact of the die to the first die pad of the patterned conductive layer, where the first die contact is disposed on an active surface of the die; and electrically connecting a second die contact of the die to the second die pad of the patterned conductive layer, where the second die contact is disposed on a major surface of the die that faces the recessed surface and is opposed to the active surface. The first and second conductors of the patterned conductive layer extend between the recessed surface of the cavity and the first major surface of the carrier substrate adjacent the cavity.

In another example, aspects of this disclosure relate to a hermetically-sealed system. The system includes a housing having an inner surface and an outer surface, a device substrate hermetically sealed to the housing and having a first major surface and a second major surface, and a die carrier package disposed on the first major surface of the substrate and having a die that has an active surface facing the device substrate. The die is adapted to emit light through the first and second major surfaces of the device substrate. Further, the die is disposed within a cavity of a carrier substrate of the package. The die also includes a first die contact disposed on the active surface of the die and a second die contact disposed on a major surface of the die that faces a recessed surface of the cavity of the die carrier package and that is opposed to the active surface. The first die contact is electrically connected to a first package contact disposed on a first major surface of the carrier substrate of the package adjacent the cavity and the second die contact is electrically connected to a second package contact disposed on the first major surface of the carrier substrate of the package adjacent the cavity. Further, the first and second package contacts are disposed between the first major surface of the carrier substrate and the first and second major surface of the device substrate. The system also includes a detector disposed on the first major surface of the substrate and has a detecting surface. The detector is adapted to detect at least a portion of the light emitted by the die.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIGS. 11A-L are various schematic cross-section views of one embodiment of a method of forming an integrated circuit package, where

DETAILED DESCRIPTION

In general, the present disclosure provides various embodiments of a die carrier package and a method of forming such package. The package can include one or more dies disposed within a cavity of a carrier substrate, where a first die contact of one or more of the dies is electrically connected to a first die pad disposed on a recessed surface of the cavity, and a second die contact of one or more of the dies is electrically connected to a second die pad also disposed on the recessed surface. The first and second die pads are electrically connected to first and second package contacts respectively. The first and second package contacts are disposed on a first major surface of the carrier substrate adjacent the cavity. In one or more embodiments, the first and second package contacts and an active surface of the die are disposed such that the package can be electrically connected to a major surface of a substrate such that the active surface of the die faces the major surface and the first and second package contacts are in contact with the same major surface. In embodiments where the die is adapted to emit electromagnetic radiation from its active surface, such radiation will be emitted in a direction away from the first major surface of the carrier substrate.

Various die carrier packages that include, e.g., one or more electromagnetic radiation emitting dies and that are mountable onto a substrate such that the electromagnetic radiation is emitted through the substrate can be challenging to manufacture. Some of these packages are required to translate a wire-bondable die into a surface-mount, solderable package while also orienting an active surface of the die towards the substrate upon which the package is mounted. In such configurations, solder pads or solder bumps of the package can be disposed on a side of the package that also includes wire bond pads and other bare die components of the die. This is in contrast to typical die stacks, where the solder pads or bumps are disposed on a side of the package opposite from the wire bond pads and bare die components of the packaged die such as for a typical die stack that includes a ball grid array or most lead-frame-based packages.

Various embodiments of die carrier packages described herein can provide one or more advantages over these typical packages. For example, one or more embodiments described herein can provide a size-efficient surface-mount package that includes one or more dies (e.g., one or more electromagnetic radiation-emitting dies). In one or more embodiments, one or more of these dies can be mounted in a "marsupial" or "dead bug" configuration (i.e., on the same side of the carrier substrate as the package contacts). This configuration allows for the active surface of one or more of the dies to face the substrate upon which the package is disposed. In one or more embodiments, the die carrier package can be manufactured in an array format such that it is compatible with high-volume assembly processes and standard processing equipment. Further, disposal of the one or more dies in a cavity of the package allows for encapsulation of such dies.

Figure 1:
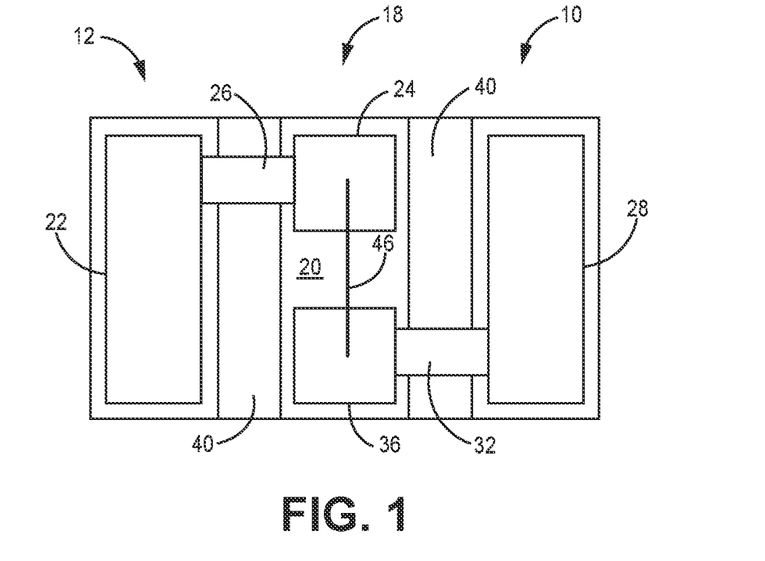
FIG. 1 is a schematic plan view of one embodiment of a die carrier package.
Figure 2:
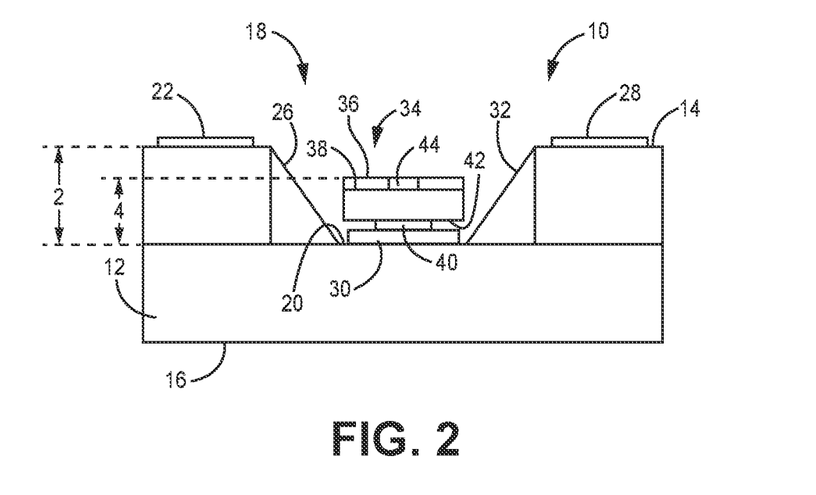
FIG. 2 is a schematic cross-section view of the die carrier package of FIG. 1.

FIGS. 1-2 are various views of one embodiment of a die carrier package 10. The package 10 includes a carrier substrate 12 that has a first major surface 14, a second major surface 16, and a cavity 18 disposed in the first major surface. The cavity 18 includes a recessed surface 20. The package 10 also includes a first package contact 22 disposed on the first major surface 14 of the carrier substrate 12 adjacent the cavity 18. As used herein, the phrase "adjacent the cavity" means that an element or component is disposed on the first major surface 14 of the carrier substrate 12 and next to but outside of the cavity 18. The first package contact 22 is electrically connected to a first die pad 24 disposed on the recessed surface 20 via a first conductor 26. The package 10 also includes a second package contact 28 disposed on the first major surface 14 of the carrier substrate 12 adjacent the cavity 18. The second package contact 28 is electrically connected to a second die pad 30 disposed on the recessed surface 20 via a second conductor 32. Further, the package 10 includes a die 34 disposed within the cavity 18 of the carrier substrate 12. The die 34 includes a first die contact 36 disposed on an active surface 38 of the die and a second die contact 40 disposed on a major surface 42 of the die that faces the recessed surface 20 and that is opposed to the active surface. The first die contact 36 is electrically connected to the first die pad 24 and the second die contact 40 is electrically connected to the second die pad 30.

The carrier substrate 12 can include any suitable material or materials, e.g., metallic, polymeric, inorganic, etc. In one or more embodiments, the carrier substrate 12 can include silicon. Further, the carrier substrate 12 can have any suitable dimensions and take any suitable shape or shapes.

The first and second major surfaces 14, 16 of the carrier substrate 12 can take any suitable shape or shapes. Disposed in the first major surface 14 is the cavity 18. The cavity 18 can take any suitable shape or shapes and have any suitable dimensions. Further, the cavity 18 can have any suitable depth 2 from the first major surface 14 of the carrier substrate 12 as measured in a direction orthogonal to the recessed surface 20 of the cavity as shown in FIG. 2. In one or more embodiments, the cavity 20 can have a depth 2 of at least 350 µm and no greater than 500 µm. In one or more embodiments, the cavity depth 2 is great than a height 4 of the die 34 as measured in the direction orthogonal to the recessed surface 20 as shown in FIG. 2. The height 4 of the die 34 includes a thickness of the second die pad 30 as measured in the direction orthogonal to the recessed surface 20. The die 34 can have any suitable height 4. In one or more embodiments, the die 34 has a height 4 of at least 100 µm and no greater than 200 µm. In one or more embodiments, the cavity depth 2 is equal to the height 4 of the die 34. Further, in one or more embodiments, the cavity depth 2 is less than the height 4 of the die 34.

The recessed surface 20 of the cavity 18 can have any suitable dimensions and take any suitable shape or shapes. In one or more embodiments, the recessed surface 20 can be parallel to the first major surface 14 of the carrier substrate 12. The cavity 18 can also include one or more side walls 40. In one or more embodiments, each sidewall 40 connects the recessed surface 20 of the cavity 18 to the first major surface 14 of the carrier substrate 12. Further, the cavity 18 can include any suitable number of sidewalls 40. As shown in FIG. 1, the cavity 18 includes two side walls 40. In one or more embodiments, the cavity 18 can include four sidewalls 40 as shown, e.g., in FIG. 3 for die carrier package 100. In the embodiment illustrated in FIGS. 1-2, the sidewalls 40 include planar portions that form an angle with the direction orthogonal to the recessed surface 20.

In one or more embodiments, a dielectric layer (not shown) can be disposed on a portion or portions of the recessed surface 20 between the first and second die pads 24, 30 and the carrier substrate. Further, a dielectric layer can also be disposed between the first and second conductors 26, 32 and the carrier substrate 12. Any suitable dielectric layer or layers can be utilized to electrically isolate one or more of the first and second die pads 24, 30 and the first and second conductors 26, 32 from the carrier substrate 12, e.g., silicon oxide, silicon nitride, tetraethyl orthosilicate (TEOS), benzocyclobutene (BCB), polyimide, etc.

The cavity 18 can be formed using any suitable technique or techniques. In one or more embodiments, the cavity 18 can be formed, e.g., by at least one of chemical etching, drilling, polishing, mechanical routing or grinding, plasma etching, molding, etc.

Disposed on the first major surface 14 of the carrier substrate 12 adjacent the cavity 20 is the first package contact 22. The first package contact 22 can include any suitable electrical contact or pad, e.g., one or more of a die pad contact, solder bump, solder ball, gold ball bump, etc. The first package contact 22 can take any suitable shape or shapes and have any suitable dimensions. The first package contact 22 can also include any suitable conductive material or materials. Further, in one or more embodiments, one or more solder bumps (e.g., solder bumps 148 of die carrier package 100 of FIGS. 3-5) can be disposed on and electrically connected to the first package contact 22.

The first package contact 22 can be electrically connected to the first die pad 24 disposed on the recessed surface 20 of the cavity 18 using any suitable technique or techniques. In one or more embodiments, the first conductor 26 electrically connects the first package contact 22 to the first die pad 24. The first conductor 26 can include any suitable conductive material or materials and be disposed in any suitable location. In one or more embodiments, one or more portions of the first conductor 26 can be disposed on at least one of the recessed surface 20 of the cavity 18, the sidewall 40, and the first major surface 14 of the carrier substrate 12. The first conductor 26 can take any suitable shape or shapes and have any suitable dimensions.

The first die pad 24 can be disposed in any suitable location on or in the recessed surface 20 of the cavity 18. Further, the first die pad 24 can include any suitable conductive material or materials. The first die pad 24 can take any suitable shape or shapes and have any suitable dimensions. Further, the first die pad 24 can be disposed on or in the recessed surface 20 using any suitable technique or techniques, e.g., photolithography, chemical vapor deposition, plasma vapor deposition, sputtering, plating, conductive ink jetting, etc.

The second package contact 28 is also disposed on the first major surface 14 of the carrier substrate 12 adjacent the cavity 18. All of the design considerations and possibilities regarding the first package contact 22 apply equally to the second package contact 28. The second package contact 28 is electrically connected to the second die pad 30 that is disposed on the recessed surface 20 of the cavity 18. Any suitable technique or techniques can be utilized to electrically connect the second package contact 28 to the second die pad 30. In one or more embodiments, the second conductor 32 electrically connects the second package contact 28 and the second die pad 30. The second die pad 30 can include any suitable die pad or contact, e.g., first die pad 24. Further, the second conductor 32 can include any suitable conductor or conductors, e.g., conductor 26.

In general, the first and second package contacts 22, 28 can be utilized to electrically connect the package 10 to any suitable device or system. For example, in one or more embodiments, the first and second package contacts 22, 28 can electrically connect the package 10 to a patterned conductive layer of a system as is further described herein. Any suitable technique or techniques can be utilized to electrically connect the first and second package contacts 22, 28 to another device or system. Although depicted as include first and second package contacts 22, 28, the package 10 can include any suitable number of package contacts.

Disposed within the cavity 18 of the carrier substrate 12 is the die 34. The die 34 can include any suitable die or device, e.g., at least one of a capacitor, resistor, passive integrated capacitor system, logic circuit, analog circuit, diode, MOSFET, insulated-gate bipolar transistor, thyristor, etc. In one or more embodiments, the die 34 can be a light emitting die. For example, the die 34 can include any electrical circuit component(s) capable of emitting light in response to an applied voltage or current, including, for example, light emitting diodes (LEDs), laser diodes, vertical cavity surface emitting lasers (VCSELs), organic LEDs printed directly on the surface, nano-emitters, etc. Further, the die 34 can be a cluster of one or more components that emit one or more discrete wavelengths or broadband emitters spanning a large range of wavelengths.

Although depicted as including one die 34, the package 10 can include any suitable number of dies as is further described herein. In one or more embodiments, the die 34 is adapted to emit electromagnetic radiation from its active surface 38. Although depicted as having one active surface 38, the die 34 can include two or more active surfaces.

In one or more embodiments, the die 34 can be a packaged light source. In one or more embodiments, the die 34 can include a flip-chip type package. In one or more embodiments, the die 34 can be a bare semiconductor die.

The die 34 can be adapted to emit light of any suitable wavelength or wavelengths. In one or more embodiments, the die 34 can emit at least one of infrared, near-infrared, visible, and UV light. In one or more embodiments, the die 34 can emit visible light having a wavelength of at least 350 nm and no greater than 950 nm. The die 34 can emit any suitable bandwidth of electromagnetic radiation. In one or more embodiments, the die 34 can emit electromagnetic radiation in a narrow band, e.g., the die is adapted to emit light having an emission bandwidth of no greater than 20 nm, 15 nm, 10 nm, or 5 nm full-width at half-maximum (FWHM). In one or more embodiments, a narrow band emitting active die can be paired with a broadband detector (e.g., detector 216 of FIG. 8) that is sensitive to most or all of the wavelengths emitted by the die. In one or more embodiments, a narrow-band emitting active die can be paired with a narrow-band detector. Further, in one or more embodiments, a narrow band emitting active die can be paired with two or more broadband detectors. For example, silicon detectors can be sensitive in the visible to near-infrared wavelength ranges (e.g., up to about 1000 nm), but gallium arsenide can be sensitive to longer infrared wavelengths (e.g., greater than 1000 nm). In one or more embodiments, a broadband emitting active die can be utilized with two or more narrow band detectors.

In one or more embodiments, the die 34 can include a broadband emitter that utilizes re-emission of phosphorous materials or combination of broadband FWHM LEDs, e.g., a 680 nm LED with greater than a 50 nm FWHM that spans into the 720 nm wavelength. In such embodiments, a single LED can provide emission at both 680 nm and 720 nm, paired with a detector that can discriminate between these two wavelengths. Similarly, a second broadband FWHM die can be used at 800 nm that also spans 760 nm. In such embodiments, two broadband FWHM dies can span four wavelengths, e.g., 680, 720, 760, and 800 nm.

In one or more embodiments, the die 34 can be adapted to emit electromagnetic radiation in one or more pulses having any suitable pulse width and periodicity. Further, in one or more embodiments, the die 34 may be pulsed in a sequential manner.

Further, the die 34 can have any suitable cone angle of emission. As used herein, the term "cone angle" refers to solid angle relative to a normal to the active surface 38 of the die. In one or more embodiments, the die 34 can have a cone angle of no greater than 90 degrees, 80 degrees, 70 degrees, 60 degrees, 50 degrees, 40 degrees, 30 degrees, 20 degrees, 10 degrees, or 5 degrees.

The die 34 includes at least one first die contact 36 disposed on the active surface 38 of the die. The first die contact 36 can include any suitable contact or pad that can provide an electrical connection to the die 34. In one or more embodiments, the first die contact 36 can include a conductive pillar (or a solder bump with a barrier metal disposed over a die pad) that can be disposed on the active surface 38 of the die 34 using any suitable technique or techniques, e.g., electroplating, etching, photo etching, solder printing, solder jetting, ball drop, etc. Any suitable solder bumps can be disposed on the first die contact 36. The first die contact 36 can have any suitable dimensions and can be disposed in any suitable arrangement or array on the active surface 38 of the die 34. Further, the first die contact 36 can include any suitable conductive material or materials.

The die 34 also includes a second die contact 40 disposed on the major surface 42 of the die that faces the recessed surface 20. Although illustrated as including one second die contact 40, the die 34 can include any suitable number of die contacts disposed on the major surface 42. The second die contact 40 can include any suitable contact or conductive pad described herein regarding first die contact 36. Further, the second die contact 40 can have any suitable dimensions and be disposed in any suitable arrangement or array on the major surface 42 of the die 34. Further, the second die contact 40 can take any suitable shape or shapes.

As mentioned herein, the die 34 is adapted to emit electromagnetic radiation from any portion or portions of its active surface 38. In one or more embodiments, the die 34 can include one or more apertures 44 through which electromagnetic radiation is emitted. The aperture 44 can be formed using any suitable technique or techniques. In one or more embodiments, a masking layer or layers can be disposed on the active surface 38 of the die 34, and the aperture 44 can be formed in the masking layer (not shown) using any suitable technique or techniques. The masking layer can include any suitable number of layers. Further, the masking layer can include any suitable material or materials, e.g., polymeric, metallic, inorganic materials, and combinations thereof.

The first die contact 36 of the die 34 can be electrically connected to the first die pad 24 using any suitable technique or techniques. In the embodiment illustrated in FIGS. 1-2, the first die contact 36 can be wire-bonded to the first die pad 24 by a wire 46 that is disposed within the cavity 18. In one or more embodiments, the die 34 and the wire 46 are disposed below a plane defined by the first major surface 14 of the carrier substrate 12. In one or more embodiments, the die 34 can include a flip-chip die that includes first and second die contacts 36, 40 disposed on the major surface 42 with no contacts disposed on the active surface 38.

Further, the second die contact 40 is electrically connected to the second die pad 30 using any suitable technique or techniques, e.g., thermocompression bonding, eutectic bonding, sintering, etc. In one or more embodiments, the second die contact 40 is disposed on the second die pad 30. In one or more embodiments, a conductive adhesive or solder can be disposed between the second die contact 40 and the second die pad 30 such that the die 34 remains disposed on the second die contact.

As mentioned herein, the first and second package contacts 22, 28, the first and second conductors, 26, 32, and the first and second die pads 24, 30 can each include any suitable conductive material or materials. In one or more embodiments, at least one of the first and second package contacts 22, 28, the first and second conductors, 26, 32, and the first and second die pads 24, 30, can include one or more metal layers. For example, in one or more embodiments, at least one of the first and second package contacts 22, 28, the first and second conductors, 26, 32, and the first and second die pads 24, 30, and can include a first metal layer and a second metal layer disposed on the first metal layer such that the second metal layer is electrically connected to the first metal layer. The first metal layer can include any suitable conductive material or materials, e.g., aluminum (Al), titanium (Ti), nickel-vanadium (NiV), etc. Further, the second metal layer can include any suitable conductive material or materials, e.g., the same materials described herein regarding the first metal layer. In one or more embodiments, the first metal layer includes the same material or materials as the material or materials of the second metal layer. In one or more embodiments, the second metal layer includes a material or materials that are different from the materials utilized to form the first metal layer.

Although not shown, the package 10 can include an encapsulant disposed in the cavity 18 over one or more portions of the die 34. In one or more embodiments, this encapsulant can completely encapsulate the die 34. In one or more embodiments, the encapsulant can also encapsulate the wire 46 that is utilized to electrically connect the first die contact 36 to the first die pad 24. Any suitable encapsulant or encapsulants can be utilized, e.g., a thermosetting epoxy resin that includes inorganic filler particles, an (reflowable) epoxy film that is laminated to the die in wafer form to fill the cavities level to the surface of the wafer 34 or over the top of the cavity, silicone (e.g., an optically-clear encapsulant that is typically used in electronics assembly), etc.

Figure 3:
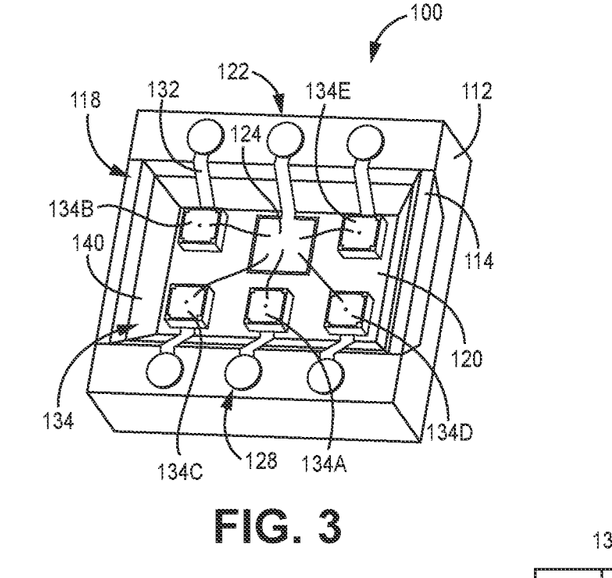
FIG. 3 is a schematic perspective view of another embodiment of a die carrier package.
Figure 4:
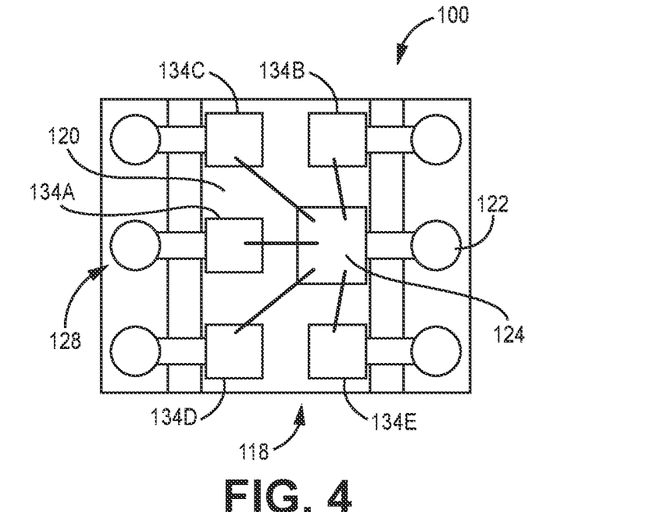
FIG. 4 is a schematic cross-section view of the die carrier package of FIG. 3.
Figure 5:
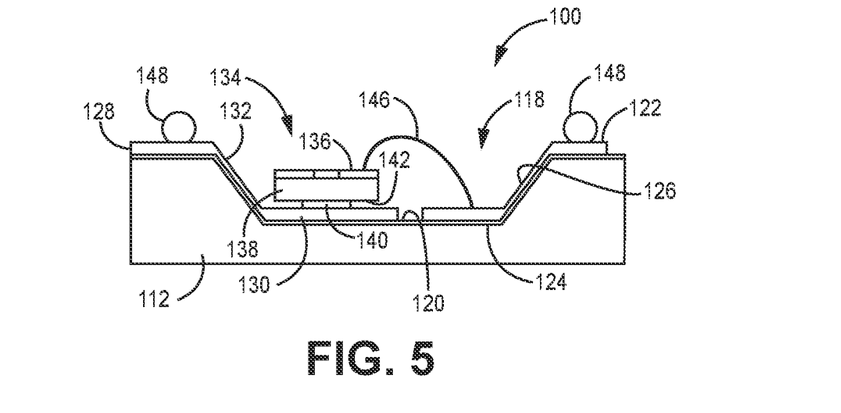
FIG. 5 is a schematic cross-section view of the die carrier package of FIG. 3.

The various embodiments of die carrier packages described herein can include any suitable number of dies disposed in any suitable relationship on a carrier substrate. For example, FIGS. 3-5 are various views of another embodiment of a die carrier package 100. All of the design considerations and possibilities regarding the die carrier package 10 of FIGS. 1-2 apply equally to the die carrier package 100 of FIGS. 3-5.

One difference between package 100 of FIGS. 3-5 and package 10 of FIGS. 1-2 is that the package 100 includes two or more dies (collectively referred to as dies 134) disposed within cavity 118 of carrier substrate 112. The package 100 can include any suitable number of dies 134, e.g., 1, 2, 3, 4, 5, 6, or more dies disposed on the carrier substrate 112. In general, the number of active dies and corresponding emission wavelengths utilized in the packages described herein can be selected according to the requirements of a particular application and will depend on the physiological condition or conditions being monitored.

As shown in FIGS. 3-5, the package 100 includes five dies 134 disposed within the cavity 118. Each die 134 includes a first die contact 136 (FIG. 5) disposed on an active surface 138 of the die and a second die contact 140 disposed on a major surface 142 of the die that faces a recessed surface 120 of the cavity and that is opposed to its active surface. Each first die contact 136 of each die 134 is electrically connected to a common first die pad 124, and each second die contact 140 is electrically connected to a second die pad 140 using any suitable technique or techniques. As shown in FIG. 5, the first die contact 136 of each die 134 is wire bonded to the first die pad 124 by a wire 146. As is also shown in FIG. 5, each second die contact 140 is electrically connected to the second die pad 130 by being disposed on the second die pad.

The first die pad 124 can be electrically connected to a first package contact 122 using any suitable technique or techniques. In the embodiment illustrated in FIGS. 3-5, the first die pad 124 is electrically connected to the first package contact 122 by conductor 126. Further, each second die pad 130 can be electrically connected to a second package contact 128 using any suitable technique or techniques. In one or more embodiments, each second die pad 130 is electrically connected to a second package contact 128 by a conductor 132. Further, one or more of the second package contacts 128 can include solder bumps 148 that are electrically connected to the second package contact using any suitable technique or techniques. Solder bumps 148 can be utilized to electrically connect the die carrier package 100 to any suitable device or system as is further described herein.

As mentioned herein, the die carrier package 100 of FIGS. 3-5 includes two or more dies 134 disposed in any suitable arrangement on the carrier substrate 112. Specifically, the package 100 includes five dies 134A-E disposed within the cavity 118 of the carrier substrate 112. As shown in FIG. 5, first die 134A is disposed within the cavity 118 of the carrier substrate 112 and includes a first die contact 136 disposed on an active surface 138 of the die and a second die contact 140 disposed on a major surface 142 of the die that faces the recessed surface and that is opposed to the active surface.

The first die contact 136 is electrically connected to the first die pad 124 by wire 146, and the second die contact 140 is electrically connected to the second die pad 130. Similarly, second, third, fourth, and fifth dies 134B-E are electrically connected to the first die pad 124 and respective second die pads 130 using any suitable technique or techniques. Each of the second die pads for the respective second, third, fourth, and fifth dies 134B-E are electrically connected to second package contacts 128 using any suitable technique or techniques.

Each of the active dies 134 are adapted to emit electromagnetic radiation from one or more surfaces of each die. For example, in one or more embodiments, active die 134A can be adapted to emit electromagnetic radiation that includes a first wavelength or wavelength band, active die 134B can be adapted to emit electromagnetic radiation that includes a second wavelength or wavelength band, third active die 134C can be adapted to emit electromagnetic radiation that includes a third wavelength or wavelength band, fourth active die 134D can be adapted to emit electromagnetic radiation that includes a fourth wavelength or wavelength band, and fifth active die 134E can be adapted to emit electromagnetic radiation from a top surface 122 that includes a fifth wavelength or wavelength band.

Another difference between the package 100 of FIGS. 3-5 and package 10 of FIGS. 1-2 is that the cavity 118 includes four sidewalls 140 that each connect the recessed surface 120 of the cavity to the first major surface 114 of the carrier substrate 112. The sidewalls 140 can take any suitable shape or shapes and have any suitable dimensions. Further, such sidewalls 140 can be formed using any suitable technique or techniques. In one or more embodiments, a metal layer or layers can be disposed on one or more portions of the sidewalls 140 to provide reflective structures. Although illustrated as including for sidewalls 140, the cavity 118 of the package 100 can include any suitable number of sidewalls.

Figure 12:
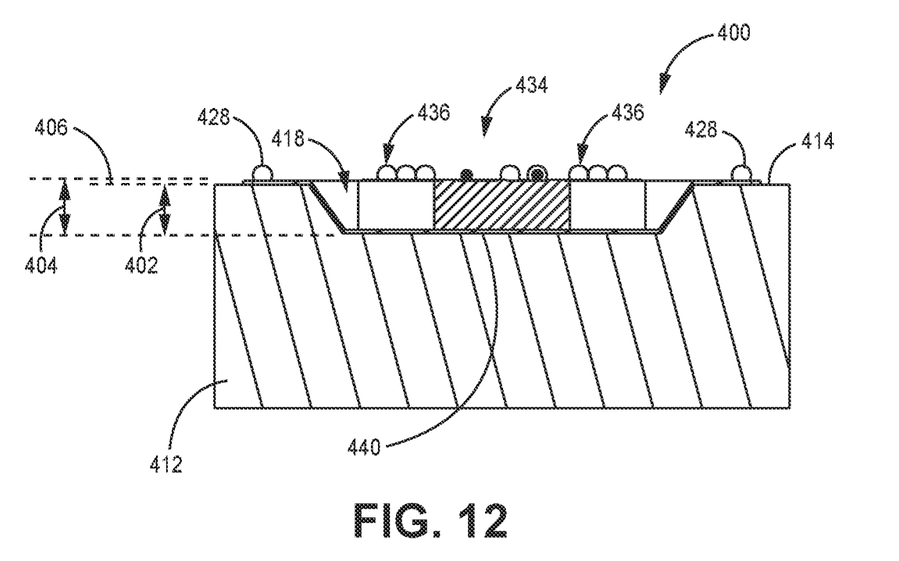
FIG. 12 is a schematic cross-section view of another embodiment of a die carrier package.

In one or more embodiments, the dimensions of the cavity, the die, and the die contacts can be selected such that the first die contact of the die is disposed above the cavity and can be electrically connected directly to one or more conductors on a substrate without the need for a first die pad and first package contact. For example, FIG. 12 is a schematic cross-section view of another embodiment of a die carrier package 400. All of the design considerations and possibilities regarding the die carrier package 10 of FIGS. 1-2 and the die carrier package 100 of FIGS. 3-5 apply equally to the die carrier package 400 of FIG. 12. One difference between package 400 and package 10 is that a height 404 of die 434, a depth 402 of cavity 418, and dimensions of first die contacts 436 are selected such that the first die contacts are disposed above a plane 406 defined by a first major surface 414 of carrier substrate 412. As a result, the first die contacts 436 and package contacts 428 (which are electrically connected to second die contact 440 via a second die pad (not shown)) can be directly connected to one or more conductors disposed on a substrate (e.g., conductors 226 disposed on a first major surface 210 of substrate 204 of FIG. 10). Unlike first die contacts 36 of die 34 of FIG. 1, the first die contacts 436 of die 434 are not electrically connected to a first die pad that is in turn electrically connected to one or more package contacts.

The various embodiments of integrated circuit packages described herein can be utilized in any suitable device or system. For example, FIGS. 6-10 are various schematic views of one embodiment of a hermetically-sealed system 200. The system 200 includes a housing 202 and a substrate 204. The housing 202 includes an inner surface 206 and an outer surface 208. The substrate 204 can be a non-conductive substrate and includes a first major surface 210 and a second major surface 212. The system 200 can also include one or more electronic devices 214 disposed within the housing 202. For example, the electronic devices 214 can include the integrated circuit package 10 of FIGS. 1-2 or integrated circuit package 100 of FIGS. 3-5. Although depicted as including integrated circuit package 100, the system 200 can include any suitable integrated circuit package. In one or more embodiments, the integrated circuit package 100 can be disposed on the first major surface 210 of the substrate 204. The integrated circuit package 100 can be adapted to emit electromagnetic radiation through the first and second major surfaces 210, 212 of the substrate 204.

Figure 8:
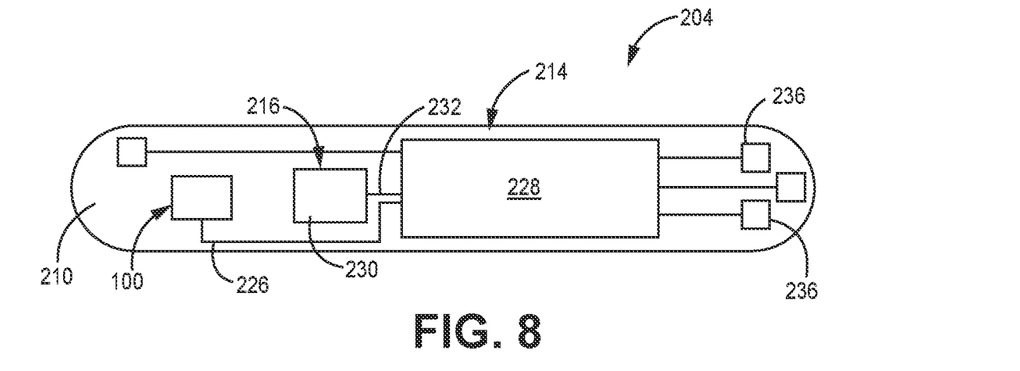
FIG. 8 is a schematic bottom plan view of a substrate of the hermetically-sealed system of FIG. 6.
Figure 9:
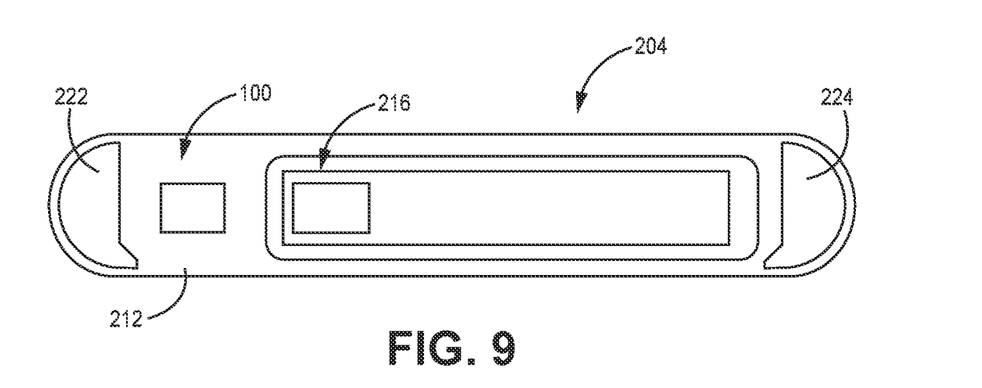
FIG. 9 is a schematic top plan view of the substrate of the hermetically-sealed system of FIG. 6.

The electronic devices 214 can further include a detector 216 (FIG. 8). In one or more embodiments, the detector 216 can be disposed on the first major surface 210 of the substrate 204. The detector 216 can be adapted to detect the electromagnetic radiation emitted by the integrated circuit package 100 that is transmitted through the substrate 204 and reflected by an object or objects back through the substrate. Together, the integrated circuit package 100 and the detector 216 can, in one or more embodiments, provide an optical sensor.

Figure 6:
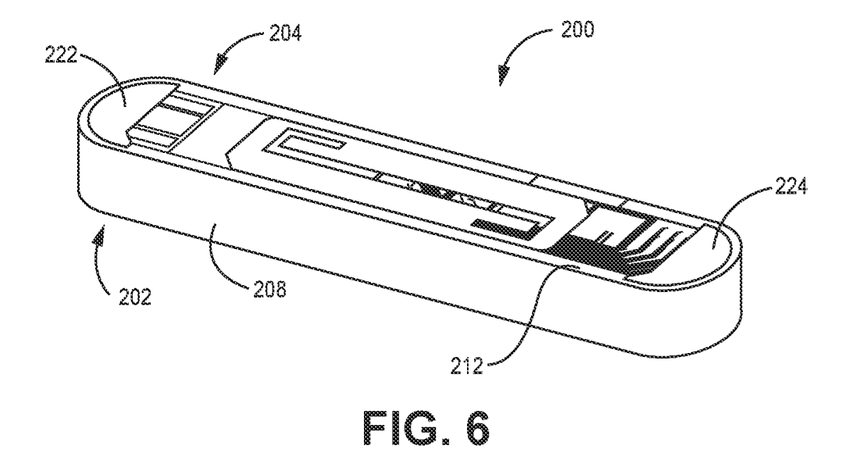
FIG. 6 is a schematic perspective view of one embodiment of hermetically-sealed system that includes the integrated circuit package of FIG. 3.
Figure 7:
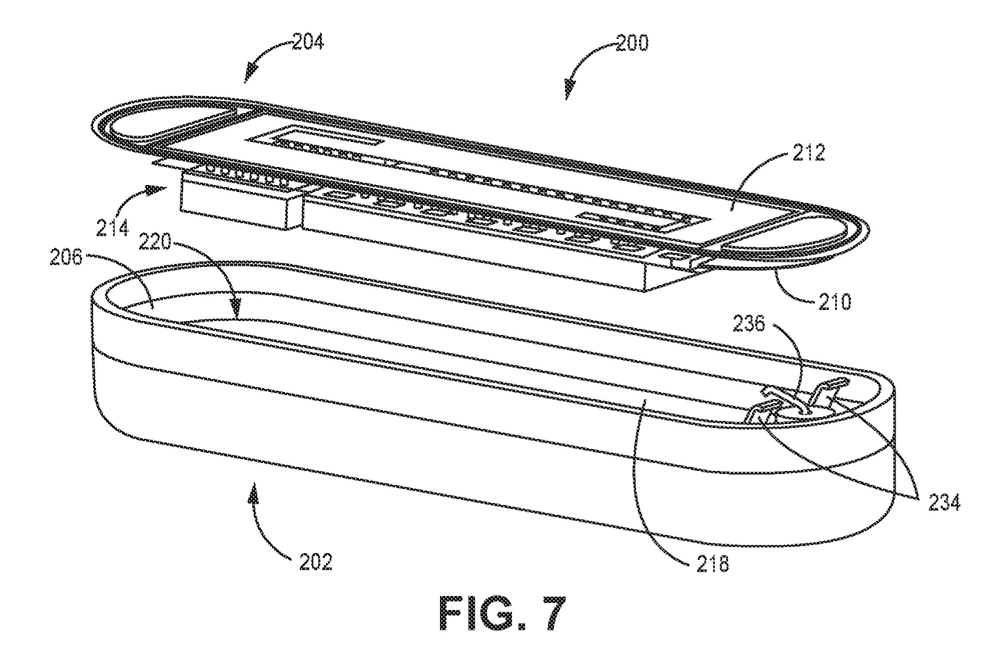
FIG. 7 is a schematic exploded view of the hermetically-sealed system of FIG. 6.

The package 200 also includes a power source 218 that is disposed at least partially within the housing 202. In one or more embodiments, the power source 218 can be disposed within a cavity 220 of the housing 202. The power source 218 can include any suitable power source or sources as is further described herein. Further, the power source can be electrically connected to the electronic devices 214 using any suitable technique or techniques. For example, in one or more embodiments, the power source 218 can include one or more power sources contacts 234, 236 that can be electrically connected to one or more device contacts 236 when the substrate 204 is sealed to the housing 202 using any suitable technique or techniques.

The substrate 204 can be sealed to the housing 202 using any suitable techniques or techniques. In one or more embodiments, the substrate 204 can be hermetically sealed to the housing 202. In one or more embodiments, the substrate 204 can be hermetically sealed to the housing 202 by a laser bond.

The housing 202 can include any suitable material or materials, e.g., metallic, polymeric, ceramic, or inorganic materials. In one or more embodiments, the housing 202 can include at least one of glass, quartz, silica, sapphire, silicon carbide, titanium, and diamond. In one or more embodiments, the housing 202 can include at least one of copper, silver, titanium, niobium, zirconium, tantalum, stainless steel, platinum, and iridium. The housing 202 can include the same material or combination of materials as the substrate 204. In one or more embodiments, the housing 202 can include one or more materials that are different from the material or materials of the substrate 204. Further, in one or more embodiments, the housing 202 can include biocompatible materials such that the system 200 can be implanted within a patient's body. For example, one or more coatings or layers can be disposed on the outer surface 208 of the housing 202 that provide biocompatibility. In one or more embodiments, the housing 202 can be electrically conductive to provide a ground electrode for the system 200 as is known in the art. In one or more embodiments, the housing 202 can be nonconductive.

Further, the housing 202 can take any suitable shape or shapes and can have any suitable dimensions. In one or more embodiments, the housing 202 takes a shape that forms the cavity 220 that can accommodate the power source 218 (including active material and power source electronics) and one or more electronic devices 214 as is further described herein.

Sealed to the housing 202 is the substrate 204. In one or more embodiments, the substrate 204 can be a non-conductive or insulative substrate such that the electronic devices 214 (including integrated circuit package 100 and detector 216), optional external electrodes 222, 224 and any conductors or other devices disposed on the substrate can be electrically isolated if desired. The substrate 204 can include any suitable material or materials. In one or more embodiments, the substrate 204 can include at least one of glass, quartz, silica, sapphire, silicon carbide, diamond, and gallium nitride. As with the housing 202, the substrate 204 can include a biocompatible material. For example, the substrate 204 can include one or more coatings or layers that can provide biocompatibility.

In one or more embodiments, the substrate 204 can be a transparent substrate. As used herein, the phrase "transparent substrate" refers to a substrate that can transmit a given percentage of electromagnetic radiation incident thereon during use of laser bonding techniques described herein to preferentially heat only an outer surface of the substrate (e.g., first major surface 210 or second major surface 212 of substrate 204), and not an inner bulk of the substrate, and thereby create a bond that has a relatively greater strength than the bulk strength of the substrate. Further, the transparent substrate 204 can transmit light emitted by the integrated circuit package 100 having any suitable wavelength or combinations of wavelengths. The substrate 204 can be substantially transparent at a desired wavelength or range of wavelengths. As used herein, the phrase "substantially transparent" means that the substrate 204 transmits greater than 50% of light incident on the substrate for a selected wavelength or range of wavelengths, assuming no reflection at the air-substrate boundaries. In one or more embodiments, the substrate 204 can be substantially transmissive to light having a wavelength of at least 200 nm. In one or more embodiments, the substrate 30 can be substantially transmissive to light having a wavelength of greater than 10,000 nm. In one or more embodiments, the substrate 204 can be substantially transmissive to light having a wavelength in a range of 200 nm to 10,000 nm. In one or more embodiments, the substrate 204 can be substantially transmissive to at least one of UV light, visible light, and IR light.

In one or more embodiments, at least a portion of the substrate 204 can be transparent such that the detector 216 disposed on the first major surface 210 of the substrate can detect one or more external signals, e.g., from a patient, when the system 200 is disposed within the patient. In one or more embodiments, the at least a portion of the substrate 204 can be sufficiently transparent to enable transmission of all, or a sufficient magnitude, of the electromagnetic radiation that is incident on the substrate for reception by the detector 216 such that the received electromagnetic radiation can be processed to detect the external signal. In one or more embodiments, the substrate 204 can be opaque, and a through-hole can be formed through the substrate and filled with a transparent hermetic material such as glass to provide a transparent portion of the substrate.

The substrate 204 can include any suitable dimensions, e.g., thicknesses. Further, the substrate 204 can take any suitable shape or combinations of shapes. In one or more embodiments, the substrate 204 can take a shape or combination of shapes that is complementary to a shape of the housing 202 such that the substrate can be sealed to the housing and provide a low-profile shape for the system 200. Further, the substrate 204 can be a single, unitary substrate or multiple substrates joined together.

Disposed on the first major surface 210 of the substrate 204 are the electronic devices 214. Although depicted as being disposed on the first major surface 210, one or more electronic devices 214 can be disposed on the second major surface 212, or one or more electronic devices can be disposed on both the first and second major surfaces. In one or more embodiments, one or more electronic devices 214 can be disposed within the housing 204 and not connected to the substrate 202. The electronic devices 214 can include any suitable circuit or component, e.g., capacitors, transistors, integrated circuits, including controllers and multiplexers, sensors, light sources, detectors, accelerometers, signal processors, etc.

Further, any suitable technique or techniques can be utilized to dispose one or more electronic devices 214 on the substrate 204 and/or within the cavity 220 of the housing 202. In one or more embodiments, one or more electronic devices 214 can be formed on the first major surface 210 of the substrate 204. In one or more embodiments, one or more devices 214 can be formed separately and then connected to the first major surface 210. Any suitable technique or techniques can be utilized to connect the electronic devices 214 to the substrate 204, e.g., a bond can be formed between the electronic device and the first major surface 210 of the substrate. The electronic devices 214 can include one or more integrated circuit packages 10 each having any suitable number of active dies.

Figure 10:
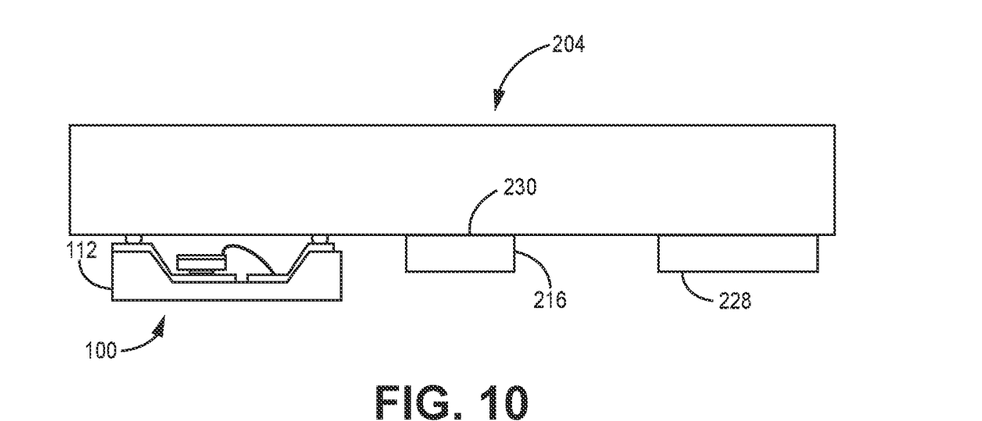
FIG. 10 is a schematic cross-section view of the substrate of the hermetically-sealed system of FIG. 6.

Although depicted as including a single integrated circuit package 100, the system 200 can include any suitable number of integrated circuit packages. The integrated circuit package 100 can be disposed in any suitable location within the housing 202 of the system 200. In one or more embodiments, the integrated circuit package 100 is disposed adjacent the first major surface 210 of the substrate 204. As used herein, the term "adjacent" means that an element or component is disposed closer to the first major surface 210 of the substrate 204 than to the power source 218 disposed within the housing 202. In one or more embodiments, the integrated circuit package 100 can be disposed on the first major surface 210 of the substrate 204 as shown in FIG. 10 using any suitable technique or techniques. In such embodiments, one or more first and second package contacts 122, 128 of the package 100 can be electrically connected to one or more conductors 226 (FIG. 8) disposed on the first major surface 210 of the substrate 204 using any suitable technique or techniques, e.g., bump bonding, solder reflow, conventional wire bonding, laser ribbon bonding, conductive epoxy bonding, etc.

The integrated circuit package 100 can be electrically connected to one or more electronic devices 214 disposed on one or both of the first major surface 210 and second major surface 212 of the substrate 204 or within the housing 202 using any suitable technique or techniques. For example, the integrated circuit package 100 can be electrically connected to the conductor 226 (FIG. 8) that is disposed on or within the substrate 204. The conductor 226 can electrically connect the integrated circuit package 100 to a controller 228 of the electronic devices 214. In one or more embodiments, a patterned conductive layer (not shown) can be disposed on the first major surface 210 of the substrate 204. In such embodiments, the first and second package contacts 122, 128 of the integrated circuit package 100 can be electrically connected to the patterned conductive layer disposed on the first major surface 210 of the substrate 204 using any suitable technique or techniques.

The system 200 also includes the detector 216. The detector 216 includes a detecting surface 230 (FIG. 10). The detector 216 can include any suitable detector that is adapted to detect electromagnetic radiation emitted by the integrated circuit package 10, e.g., one or more photodiodes, photoresistors or light dependent resistors, phototransistors, photovoltaic cells, charge-coupled devices, avalanche detectors, etc. In one or more embodiments, the integrated circuit package 100 can also be utilized as a detector. Although depicted as including a single detector 216, the system 200 can include any suitable number of detectors. For example, the system 200 can include a second detector (not shown) disposed on the first major surface 210 of the substrate 204. In one or more embodiments, the detector 216 can be adapted to detected electromagnetic radiation emitted, e.g., by the first die 134A of the integrated circuit package 100 and the second detector can be adapted to detected electromagnetic radiation emitted, e.g., by the second die 134B of the integrated circuit package.

The detector 216 can be adapted to detect any desired wavelength or wavelengths of electromagnetic radiation. In one or more embodiments, the detector 216 can detect one or more of infrared, near-infrared, visible, and UV light. In one or more embodiments, the detector 216 can detect visible light having a wavelength of at least 350 nm and no greater than 950 nm.

The detector 216 can be disposed in any suitable location within the housing 202 of the system 200 or outside of the housing (e.g., on the second major surface 212 of the substrate 204). In one or more embodiments, the detector 216 is disposed adjacent the first major surface 210 of the substrate 204. In one or more embodiments, the detector 216 can be disposed on the first major surface 210 of the substrate 204 using any suitable technique or techniques as shown in FIG. 10. In such embodiments, the detecting surface 230 can be connected to the first major surface 210 of the substrate 204 using any suitable technique. For example, in one or more embodiments, the detecting surface 230 can be disposed on the first major surface 210 of the substrate 204 using an optical coupling layer. Any suitable coupling layer can be utilized. In one or more embodiments, the optical coupling layer can include an optical adhesive. In one or more embodiments, the detector 216 can be electrically connected to an electrode disposed on a carrier. The detector 216 can also be wired bonded from the integrated circuit package 100 to a second electrode on the carrier. The carrier can be designed such that the two electrodes are in a single plane. the carrier can then be bump-bonded to one or more conductors (e.g., conductor 232) disposed on the substrate 204.

The detector 216 can be electrically connected to one or more of the other electronic devices 214 disposed on one or both of the first major surface 210 and second major surface 212 of the substrate 204 or within the housing 202 using any suitable technique or techniques. For example, the detector 216 can be electrically connected to the conductor 232 that is disposed on or within the substrate 204. In one or more embodiments, the conductor 232 can electrically connect the detector 218 to the controller 228 of the electronic devices 214. Any suitable technique or techniques can be utilized to electrically connect the detector 218 to the conductor 232.

The various embodiments of systems described herein can be utilized to determine one or more physiological conditions. Any suitable physiological condition can be determined, e.g., heart rate, arterial blood oxygen level (SpO2), blood flow, fluid volume (e.g., edema), tissue oxygen saturation (StO2), perfusion index (PI), Total Hemoglobin/Hematocrit, Tissue Hemoglobin Concentration Index (THI), venous oxygen saturation (SvO2), ambient light level within a patient, respiration rate, optically interrogated biochemical sensors (e.g., fluorescent or other coatings and materials in contact with tissue), pulse wave velocity (e.g., pulse transit time), etc.

Further, the various embodiments of integrated circuit packages described herein can be manufactured using any suitable technique or techniques. For example, FIGS. 11A-L are various cross-section views of one method 300 of forming integrated circuit package 100. Although described in reference to integrated circuit package 100 of FIGS. 3-5, the method 300 can be utilized to form any suitable integrated circuit package.

Figure 11A:
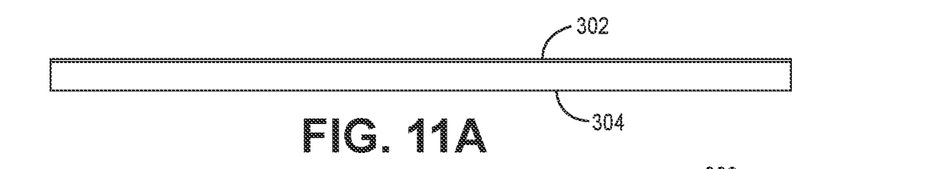
FIG. 11A is a schematic cross-section view of disposing an insulative layer on a carrier substrate wafer.
Figure 11B:
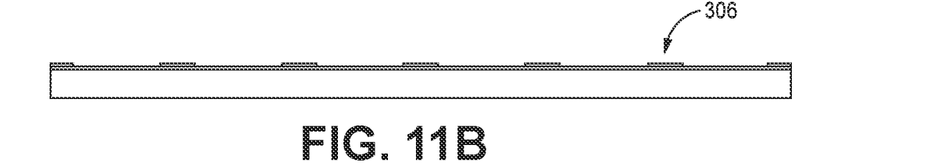
FIG. 11B is a schematic cross-section view of disposing a mask on the insulative layer.

As shown in FIG. 11A, an insulative layer 302 can be disposed on a carrier substrate wafer 304 using any suitable technique or techniques. The insulative layer 302 can include any suitable material or materials, e.g., silicon dioxide, organic dielectric materials, etc. A photoresist layer 306 can be disposed on the insulative layer 302 using any suitable technique or techniques as shown in FIG. 11B. The photoresist layer 306 can include any suitable material or materials. Further, the photoresist layer 306 can be patterned in any suitable pattern using any suitable technique or techniques.

Figure 11C:
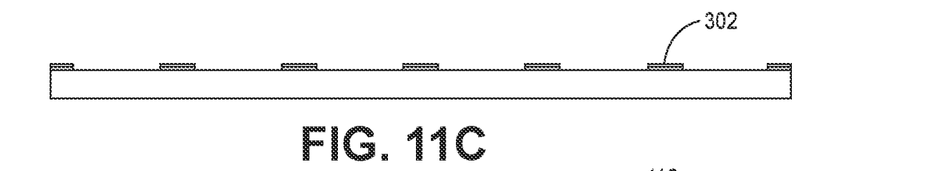
FIG. 11C is a schematic cross-section view of patterning the insulative layer.
Figure 11D:
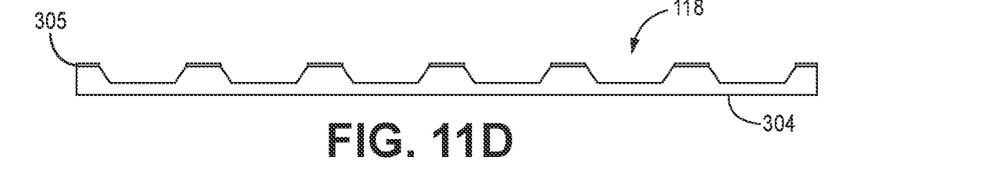
FIG. 11D is a schematic cross-section view of forming a cavity in a first major surface of the carrier substrate wafer.
Figure 11E:
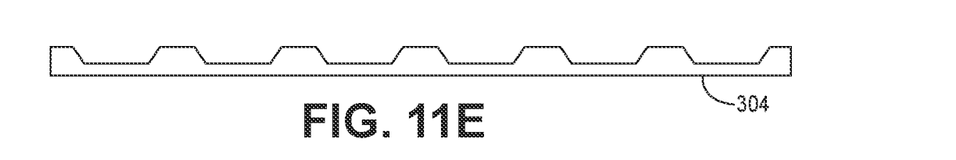
FIG. 11E is a schematic cross-section view of removing the insulative layer.

As shown in FIG. 11C, the insulative layer 302 can be etched through the patterned photoresist layer 306 using any suitable technique or techniques. Following etching of the thermal insulative layer 302, the carrier substrate wafer 304 can be etched using any suitable technique or techniques to form cavities 118 in the carrier substrate wafer as shown in FIG. 11D. In one or more embodiments, a cavity depth of each of the cavities 118 can be of sufficient dimensions to contain the die 134 and wires 146 without extending through a plane of a major surface 305 of the carrier substrate wafer 304. In FIG. 11E, the thermal insulative layer 302 is removed from the carrier substrate wafer 304 using any suitable technique or techniques.

Figure 11F:
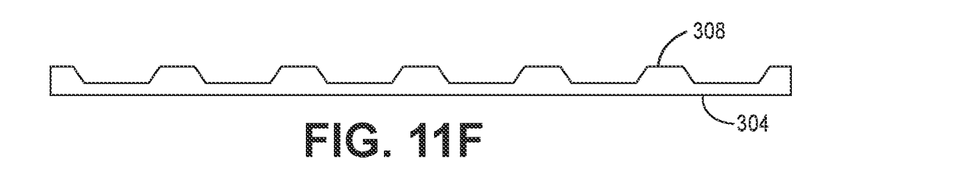
FIG. 11F is a schematic cross-section view of disposing a second insulative layer on the carrier substrate wafer.
Figure 11G:
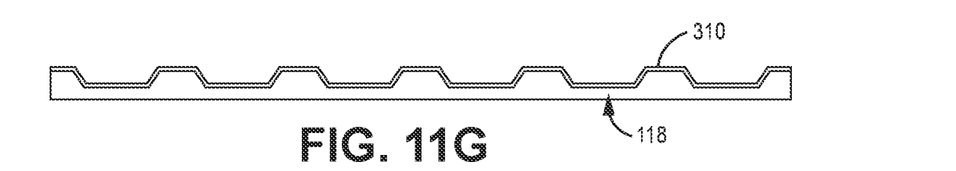
FIG. 11G is a schematic cross-section view of disposing conductive material on the carrier substrate wafer.

A second insulative layer 308 can be disposed on one or more portions of the carrier substrate wafer 304 as shown in FIG. 11F using any suitable technique or techniques. A metal layer 310 can be disposed on one or more portions of the second insulative layer 308 using any suitable technique or techniques as shown in FIG. 11G. In one or more embodiments, the metal layer 310 can be sputtered onto the second insulative layer 308. Any suitable conductive material or materials can be utilized for conductive material 310, e.g., aluminum, silver, copper, gold, etc.

Figure 11H:
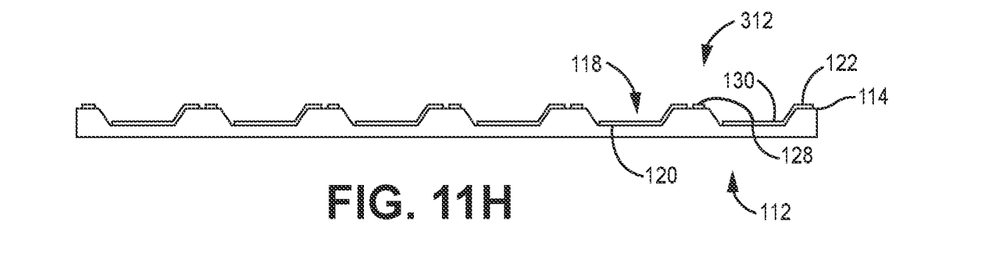
FIG. 11H is a schematic cross-section view of patterning the conductive material to form a patterned conductive layer.

The metal layer 310 can be patterned as shown in FIG. 11H to provide a patterned conductive layer 312 on the recessed surface 118 of each cavity 118 and the major surface 305 of the carrier substrate wafer 304 using any suitable technique or techniques. Although not shown for clarity, one or more portions of the second insulative layer 308 can remain disposed between the patterned conductive layer 312 and the carrier substrate wafer 304. The patterned conductive layer 312 includes first and second package contacts 122, 128 disposed on the first major surface 114 of each carrier substrate 112 adjacent the cavity 118 and first and second die pads 124, 130 (FIG. 5) disposed on the recessed surface 120 of the cavity. As is further shown in FIG. 5, the first package contact 122 is electrically connected to the first die pad 124 by the first conductor 126, and the second package contact 128 is electrically connected to the second die pad 130 by the second conductor 132.

In one or more embodiments, the conductive material 310 that is utilized to form the patterned conductive layer 312 can include two or more metal layers. For example, in one or more embodiments, the conductive material 310 can include a first metal layer of titanium, a second metal layer of nickel vanadium, and a third metal layer of gold. In one or more embodiments, the patterned conductive layer 312 can be formed by disposing a first metal layer on at least a portion of the recessed surface 120 of each cavity 118 and the first major surface 114 of each carrier substrate 112. At least a portion of the first metal layer can be patterned using any suitable technique or techniques. A dielectric layer can be disposed on the first metal layer, and a second metal layer can then be disposed on the dielectric layer and the patterned first metal layer, and at least a portion of the second metal layer can be pattern such that the patterned portion the first metal layer is registered with the patterned portion of the second metal layer.

Figure 11I:
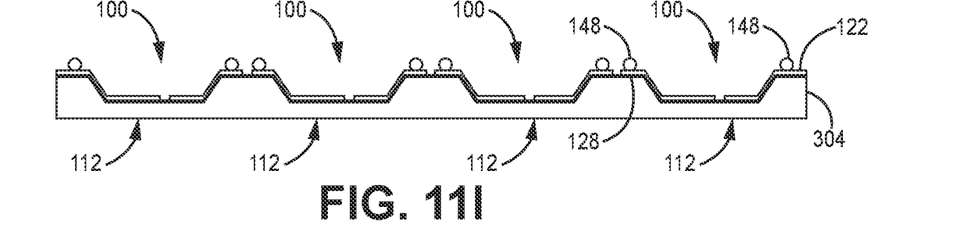
FIG. 11I is a schematic cross-section view of disposing solder bumps on at least one of first and second package contacts.

In one or more embodiments, one or more solder bumps 148 can be disposed on one or both of the first and second package contacts 122, 128 of each carrier substrate 112 using any suitable technique or techniques as shown in FIG. 11I. Any suitable solder bumps 148 can be utilized. In one or more embodiments, the solder bumps 148 are adapted to electrically connect the individual die carrier packages 100 to a device or system as is further described herein.

Figure 11J:
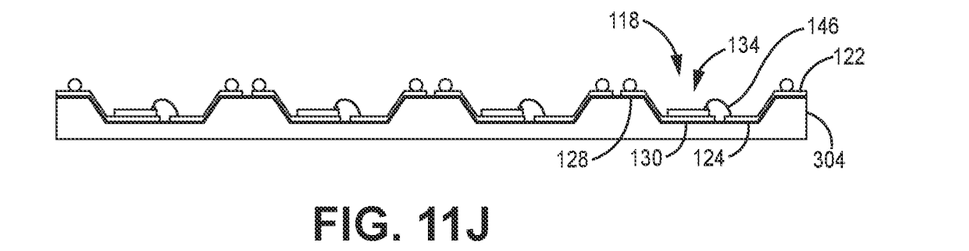
FIG. 11J is a schematic cross-section view of disposing a die within each cavity of the carrier substrate wafer and electrically connecting a first die contact of the die to a first die pad of the patterned conductive layer and a second die contact of the die to the second die pad of the patterned conductive layer.

As shown in FIG. 11J, one or more dies 134 can be disposed within each cavity 118 that have been formed in the die carrier substrate 304 using any suitable technique or techniques, e.g., pick and place, etc. Further, any suitable technique or techniques can be utilized to attach the dies 134 to the said second die pad 130 of each cavity 118. Further, in one or more embodiments, the first die contact 136 (FIG. 5) of each die 134 can be electrically connected to the first die pad 124 using any suitable technique or techniques, e.g., by wire 146 as shown in FIG. 11J. The second die contact 140 (FIG. 5) can be electrically connected to the second die pad 130 of each cavity 118 using any suitable technique or techniques.

Figure 11K:
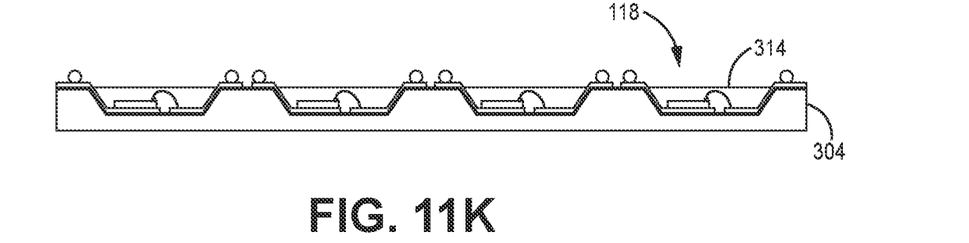
FIG. 11K is a schematic cross-section view of disposing an encapsulating material in each cavity of the carrier substrate wafer.
Figure 11L:
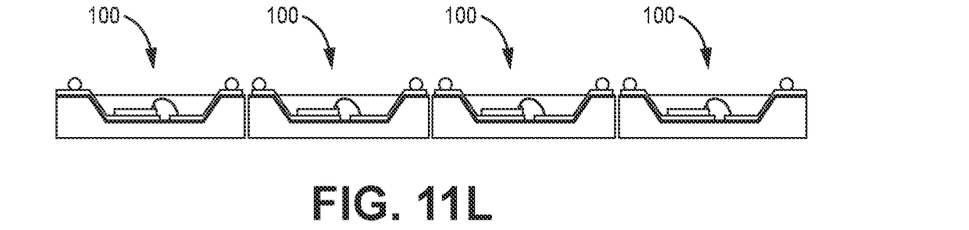
FIG. 11L is a schematic cross-section view of singulating the carrier substrate wafer to provide two or more die carrier packages.

As shown in FIG. 11K, each cavity 118 can be at least partially filled with an encapsulant 314 using any suitable technique or techniques. Further, any suitable encapsulant can be utilized to encapsulate one or more dies 134 disposed in each cavity 118 of the die carrier substrate wafer 304, e.g., a UV curable epoxy, etc. In one or more embodiments, the encapsulant 314 can be planarized using any suitable technique or techniques. Further, shown in FIG. 11L, the carrier substrate wafer 304 can be singulated using any suitable technique or techniques to provide individual die carrier packages 100.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A method of forming a die carrier package, comprising:
   forming a cavity in a first major surface of a carrier substrate, wherein the cavity comprises a recessed surface;
   forming a patterned conductive layer on the recessed surface of the cavity and the first major surface of the carrier substrate, wherein the first patterned conductive layer comprises first and second package contacts disposed on the first major surface of the carrier substrate adjacent the cavity and first and second die pads disposed on the recessed surface of the cavity, wherein the first package contact is electrically connected to the first die pad by a first conductor and the second package contact is electrically connected to the second die pad by a second conductor;
   disposing a die within the cavity, wherein the die is adapted to emit electromagnetic radiation from an active surface of the die;
   electrically connecting a first die contact of the die to the first die pad of the patterned conductive layer, wherein the first die contact is disposed on the active surface of the die; and
   electrically connecting a second die contact of the die to the second die pad of the patterned conductive layer, wherein the second die contact is disposed on a major surface of the die that faces the recessed surface and is opposed to the active surface;
   wherein the first and second conductors of the patterned conductive layer extend between the recessed surface of the cavity and the first major surface of the carrier substrate adjacent the cavity.

2. The method of claim 1, wherein forming the patterned conductive layer comprises:
disposing a first metal layer on at least a portion of the recessed surface of the cavity and the first major surface of the carrier substrate;
patterning a portion of the first metal layer;
disposing a second metal layer on the patterned first metal layer; and
patterning a portion of the second metal layer such that the patterned portion of the first metal layer is registered with the patterned portion of the second metal layer.

3. The method of claim 1, further comprising disposing solder bumps on each of the first and second package contacts.

4. The method of claim 1, further comprising disposing an encapsulant over the die and within the cavity.

5. The method of claim 1, wherein electrically connecting the first die contact to the first die pad comprises wire-bonding the first die contact to the first die pad.

6. The method of claim 1, further comprising disposing an insulative layer on the first major surface of the carrier substrate prior to forming the cavity in the first major surface of the carrier substrate.

7. The method of claim 6, further comprising disposing a photoresist layer on the insulative layer prior to forming the cavity in the first major surface of the carrier substrate.

8. The method of claim 7, further comprising etching the photoresist layer and the insulative layer prior to forming the cavity in the first major surface of the carrier substrate.

9. The method of claim 1, further comprising disposing an insulative layer on one or more portions of the carrier substrate prior to forming the patterned conductive layer.

10. The method of claim 9, wherein forming the patterned conductive layer comprises disposing a metal layer onto the insulative layer.

11. The method of claim 10, wherein disposing the metal layer comprises sputtering the metal layer onto the insulative layer.

12. The method of claim 1, wherein forming the patterned conductive layer comprises:
disposing a first metal layer on at least a portion of the recessed surface of the cavity and the first major surface of the carrier substrate;
patterning a portion of the first metal layer;
disposing a dielectric layer on the patterned first metal layer;
disposing a second metal layer on the dielectric layer and the patterned first metal layer; and
patterning a portion of the second metal layer such that the patterned portion of the first metal layer is registered with the patterned portion of the second metal layer.

13. A method comprising:
disposing a die carrier package on a first major surface of device substrate, wherein the package comprises:
a die that comprises an active surface facing the device substrate, wherein the die is adapted to emit light through the first and second major surfaces of the device substrate, wherein the die is disposed within a cavity of a carrier substrate of the package, wherein the die further comprises a first die contact disposed on the active surface of the die and a second die contact disposed on a major surface of the die that faces a recessed surface of the cavity of the die carrier package and that is opposed to the active surface, wherein the first die contact is electrically connected to a first package contact disposed on a first major surface of the carrier substrate of the package adjacent the cavity and the second die contact is electrically connected to a second package contact disposed on the first major surface of the carrier substrate of the package adjacent the cavity, wherein the first and second package contacts are disposed between the first major surface of the carrier substrate and the first and second major surfaces of the device substrate; and
disposing a detector on the first major surface of the device substrate, wherein the detector is adapted to detect at least a portion of the light emitted by the die.

14. The method of claim 13, further comprising hermetically sealing the device substrate to a housing such that the die carrier package and the detector are disposed within the housing.

15. The method of claim 14, wherein hermetically sealing the device substrate comprises laser bonding the device substrate to the housing.

16. The method of claim 15, further comprising forming an external electrode on a second major surface of the device substrate.

17. The method of claim 14, further comprising electrically connecting the first and second package contacts to a patterned conductive layer disposed on the first major surface of the device substrate.

18. A method comprising:
forming cavities in a first major surface of a carrier substrate wafer that comprises a plurality of carrier substrates, wherein the first major surface of the carrier substrate wafer forms a first major surface of each carrier substrate, wherein each cavity comprises a recessed surface;
forming a patterned conductive layer on the recessed surface of each cavity and the first major surface of the carrier substrate wafer, wherein the first patterned conductive layer comprises first and second package contacts disposed on the first major surface of each carrier substrate adjacent the cavity and first and second die pads disposed on the recessed surface of the cavity, wherein the first package contact is electrically connected to the first die pad by a first conductor and the second package contact is electrically connected to the second die pad by a second conductor;
disposing a die within each cavity, wherein each die is adapted to emit electromagnetic radiation from an active surface of the die;
electrically connecting a first die contact of each die to the first die pad of the patterned conductive layer of each carrier substrate, wherein the first die contact is disposed on the active surface of the die; and
electrically connecting a second die contact of each die to the second die pad of the patterned conductive layer of each carrier substrate, wherein the second die contact is disposed on a major surface of the die that faces the recessed surface and is opposed to the active surface;
wherein the first and second conductors of the patterned conductive layer of each carrier substrate extend between the recessed surface of the cavity and the first major surface of the carrier substrate adjacent the cavity.

19. The method of claim 18, further comprising disposing one or more solder bumps on one or both of the first and second package contacts of each carrier substrate.

20. The method of claim 18, further comprising singulating the carrier substrate wafer to provide individual die carrier packages.

* * * * *